United States Patent [19]
Adjei et al.

[11] Patent Number: 5,635,161
[45] Date of Patent: Jun. 3, 1997

[54] AEROSOL DRUG FORMULATIONS CONTAINING VEGETABLE OILS

[75] Inventors: Akwete L. Adjei, Wadsworth; Pramod K. Gupta, Gurnee; Dennis Y. Lee, Highland Park, all of Ill.

[73] Assignee: Abbott Laboratories, Abbott Park, Ill.

[21] Appl. No.: 485,222

[22] Filed: Jun. 7, 1995

[51] Int. Cl.$^6$ .................................................. A61K 9/12
[52] U.S. Cl. ............................ 424/45; 424/46; 514/937
[58] Field of Search .............................. 424/43, 45, 46; 514/937

[56] References Cited

U.S. PATENT DOCUMENTS

| | | | |
|---|---|---|---|
| 3,869,549 | 3/1975 | Geller | 514/937 |
| 4,851,211 | 7/1989 | Adjei et al. | 424/47 |
| 4,897,256 | 1/1990 | Adjei et al. | 424/45 |
| 5,202,110 | 4/1993 | Dalby et al. | 424/45 |
| 5,225,183 | 7/1993 | Purewal et al. | 424/45 |
| 5,230,884 | 7/1993 | Evans et al. | 424/45 |
| 5,419,315 | 5/1995 | Rubsamen | 128/200.14 |

FOREIGN PATENT DOCUMENTS

| | | | |
|---|---|---|---|
| 0510731 | 10/1992 | European Pat. Off. | 424/45 |
| 9111173 | 8/1991 | WIPO . | |
| 9200061 | 1/1992 | WIPO . | |
| 9200107 | 1/1992 | WIPO . | |
| 9208447 | 5/1992 | WIPO . | |
| 9214444 | 9/1992 | WIPO . | |
| 9504541 | 2/1995 | WIPO . | |

OTHER PUBLICATIONS

Morén, F. et al. (1993). Aerosols in Medicine. Elsevier Science Publishing, pp. 303–319.

*Primary Examiner*—Raj Bawa
*Attorney, Agent, or Firm*—Mona Anand; Thomas D. Brainard

[57] ABSTRACT

Pharmaceutical compositions for aerosol delivery comprising (a) a medicament, (b) a non-chlorofluorocarbon propellant, and (c) a vegetable oil or a pharmaceutically acceptable derivative thereof, as well as a method for preparing such compositions in which unwanted aggregation of the medicament is prevented without the use of surfactants, protective colloids or cosolvents.

15 Claims, 5 Drawing Sheets

AEROSOL DRUG FORMULATIONS CONTAINING VEGETABLE OILS

TECHNICAL FIELD

The present invention relates to drug formulations for aerosol delivery which are compatible with halogenated alkane propellants, and especially to excipients which are useful therein. In particular, the invention relates to inhalable formulations comprising a vegetable oil in combination with a medicament and a non-chlorofluorocarbon propellant, which formulations possess a variety of advantageous properties.

BACKGROUND OF THE INVENTION

Pulmonary delivery of peptide and protein biotherapeutics (and also non-peptide drugs) is a rapidly growing area in drug delivery. To this end, aerosol preparations of such medicaments have been developed as a means of conveyance to the respiratory system. In order for aerosols to be effective, several factors must be considered in their formulation. One factor to consider is the intended application of the aerosol drug, i.e. whether the drug is intended for systemic or topical application and/or for sustained or immediate release. For example, effective systemic administration via the pulmonary route requires delivery of the drug to the deep lung (ie. alveoli) where diffusion and phagocytosis have been proposed as primary mechanisms for drug absorption. In this situation, it is preferrable that the aerosol be formulated to release particles between 1–5 μm in size in order to overcome the lung's formidable barriers to particle deposition. In contrast, larger sized particles may be suitable for topical application of a drug where deposition of a drug in the central airways may be warranted. Other factors such as particle aggregation and drug stability must also be considered in the formulation development.

Aerosols are generally described as dispersions of medicament in a continuous phase. Preparations currently in use include both suspension and solution aerosol formulations. Suspension aerosols contain solid particles of a medicament of interest. The particles of the suspension must be pre-milled to a particular size during formulation and these particles are released upon use. In contrast, solution aerosols contain dissolved medicaments which are released from the dispenser in the form of a mist. Due to the large surface area of mist, the propellant or continuous phase (i.e. the formulation component in which the drug is either dispersed or solubilized) evaporates almost instantly leaving the residual medicament in the form of solid particles. Both suspension and solution aerosols have been used effectively to deliver certain medicaments systemically, examples being ergotamine tartrate, deoxyribonuclease and leuprolide acetate. Solution aerosols, however, have certain advantages over suspension aerosols in that they form finer particles (that can more readily reach the alveoli), they avoid the need for complex milling steps and they are cheaper to manufacture. In other cases, suspension aerosols may be more advantageous, by offering better chemical stability than their equivalent solution aerosols (possibly due to reduced oxidative or hydrolytic reactions in the formulation). Thus, there is a need for both solution and suspension aerosols depending on the intended use of the medicament contained therein as well as its chemical and physical properties.

In pressurized aerosols, also referred to as metered dose inhalers (MDIs), a physiologically inert propellant of high vapor pressure, generally a halogenated alkane, is used to discharge a medication. Use of an appropriate formulation-compatible metering valve allows delivery of precise amount of medication with each actuation. The propellants of choice for MDI devices have historically been chlorofluoro-carbons, such as Propellant 11 (trichlorofluoromethane), Propellant 12 (dichlorodifluoromethane) and Propellant 114 (dichlorotetrafluoroethane). In recent years however, there have been growing concerns that chlorofluorocarbon ("CFC") propellants have detrimental environmental effects, and in particular that they interfere with the protective upper-atmosphere ozone layer. Under an international accord (the Montreal Protocol), the use of CFC propellants phased out will be prohibited by the start of the year 1996, and possibly sooner. Alternative propellant vehicles are being developed which exhibit little or no ozone depletion potential (ODP). Such alternative propellants (referred to herein as "non-chlorofluorocarbons" ("non-CFC) or "non-chlorinated propellants) include two hydrofluorocarbons—HFC-134a (1,1,1,2-tetrafluoroethane) and HFC-227ea (1,1,1,2,3,3,3-heptafluoropropane). These propellants have negligible ODP and are currently undergoing safety and environmental testing.

Unfortunately, many surfactants which are traditionally used in MDI formulations with known CFC propellants have been found to be immiscible, and therefore incompatible, with these new, non-CFC propellants. Such surfactants are generally necessary to prevent aggregation (in the form of "caking" or crystallization, for example) of the medicinally active compound in the reservoir of the inhaler, to facilitate uniform dosing upon aerosol administration, and to provide an aerosol spray discharge having a favorable respirable fraction (that is, a particle size distribution such that a large portion of the discharge reaches the alveoli where systemic absorption takes place, and thus produces high lung deposition efficiencies). To overcome this incompatibility, it has previously been taught by Purewal et al. (EP-A-372777) to include cosolvents such as ethanol with the non-CFC propellants so as to blend the surfactants into the formulation. Another suggested approach has been to emulsify the MDI medicament in the presence of a surfactant with low-vapor pressure additives, such as polyhydroxy alcohols (for example propylene glycol).

Such cosolvents or additives may of course be physiologically active, and in some instances may not be tolerated by the user of an MDI medication. In addition, they may lead to increased instability of drug. There is therefore a need for MDI formulations compatible with non-CFC propellants which prevent aggregation of drug particles without the use of cosolvents or similar carrier additives, and which provide uniformity of dosing and a favorable respirable fraction.

Surprisingly, it has now been found that certain naturally occurring vegetable oils such as olive oil, safflower oil, soybean oil and the like are capable of stabilizing MDI formulations, especially those utilizing non-ozone-depleting propellants such as HFC-134a and HFC-227ea so as to (i) prevent aggregation of medicament, (ii) provide dosing uniformity, and (iii) afford improved lung deposition efficiency, preferably without the need for either surfactants or cosolvents. Additionally, these oils have the unexpected benefit of providing adequate lubrication for the valve used in an MDI product without the need for additional lubricants, thus aiding reliable functioning of the aerosol device throughout the life of the product. It has also been found that oils can be formulated to produce a clear solution product in the alternate non-CFC propellant either with or without additional surfactants.

Significant characteristics of vegetable oils are that: (i) they offer enhanced physical drug stability, (ii) they are non-ionic agents which do not chemically interact with drug; (iii) they have been used previously in oral and injectable liquid dosage forms, thereby establishing their physiological acceptability; (iv) they are highly soluble in HFC 134a; and (v) they may be formulated to produce either a stable suspension or a clear solution in the alternate propellant. Furthermore, solution formulations avoid the need for complex milling steps which increase the manufacturing cost of the product. Non-CFC formulations which include oils do not require the addition of (i) cosolvents like ethanol to blend the surfactant into the formulation, (ii) conventional surfactants such as sorbitan trioleate (SPAN 85™), sorbitan monooleate and oleic acid, or (iii) protective colloids like sodium lauryl sulfate and cholesterol, yet provide good lung deposition efficiencies and respirable fractions comparable to those obtained with known CFC-propellant formulations. It is thus expected that aerosol formulations comprising such oils will be useful for the delivery of both peptide and non-peptide pharmaceutical medicaments for which MDI delivery is deemed preferable.

SUMMARY OF THE INVENTION

According to one aspect of the present invention, pharmaceutical compositions are disclosed which are useful for aerosol delivery, as for example by inhalation and pulmonary absorption, comprising a therapeutically effective amount of a medicament, a halogenated alkane propellant, and a $C_{16+}$-unsaturated vegetable oil such as olive oil, safflower oil or soybean oil. The compositions may optionally comprise a sweetener such as Nutrasweet® (aspartame) an/or a taste-masking agent such as menthol. The propellants in such compositions are preferably hydrofluorocarbons and, more preferably, non-ozone depleting hydrofluorocarbons such as HFC-134a or HFC-227ea.

The medicaments to be formulated in such oil formulations include a wide variety of drugs. Preferred drugs are LHRH analogs, 5-lipoxygenase inhibitors, immunosuppressants (such as cyclosporin A, cyclosporin B, cyclosporin G, rapamycin, ascomycin and tacrolimus), antiallergens, anticholinergics and mucolytics (such as ipratropium, cromolyn and DNase), and steroids (such as flunisolide and dexamethasone) and bronchodilators. Especially preferred medicaments include leuprolide acetate, the LHRH antagonist Ac-D-2-Nal-D-4-Cl-Phe-D-3-Pal-Ser-N-MeTyr-D-Lys (Nic)-Leu-Lys(N-Isp)-Pro-D-Ala-NH$_2$ (hereinafter "D-2-Nal"), the 5-lipoxygenase inhibitor N-[3-[5-(4-fluorophenylmethyl)-2-thienyl]-1-methyl-2-propynyl]-N-hydroxyurea (hereinafter "5-LO inhibitor #1"), the immunosuppressant cyclosporin A, β-adrenergic bronchodilators such as isoproterenol, albuterol, metaproterenol, terbutaline, isoetherine, epinephrine, phenylephrine and serevent.

The vegetable oils used in the present invention may be present in a concentration of between about 0.001% and about 10% by weight, preferably in a concentration of between about 0.002% and about 5% by weight and more preferably in a concentration of between 0.01% and about 1% by weight. A sweetener such as aspartame and/or a taste-masking agent such as menthol may also be present in concentrations of between about 0.0001% and about 10% each by weight.

Particularly preferred pharmaceutical compositions embodying the present invention include those comprising leuprolide acetate or 5-LO inhibitor #1 in a concentration of between 0.05% and 5% by weight, a vegetable oil in a concentration of between 0.01% and 1% by weight, aspartame in a concentration of between 0.02% and 0.5% by weight, and menthol in a concentration of between 0.001 and 0.25% by weight.

Especially preferred pharmaceutical compositions embodying the present invention are those comprising leuprolide acetate or 5-LO inhibitor #1 in a concentration of between 0.125% and 2.5% by weight, a vegetable oil in a concentration of between 0.1% and 0.5% by weight, aspartame in a concentration of between 0.05% and 0.2% by weight, and menthol in a concentration of between 0.025 and 0.1% by weight.

Alternative, especially preferred pharmaceutical compositions embodying the present invention are those comprising 5-LO inhibitor #1 in a concentration of between 0.5% and 2% by weight, a vegetable oil in a concentration of between 0.2% and 1% by weight, aspartame in a concentration of about 0.1% by weight, and menthol in a concentration of about 0.05% by weight.

In a further aspect of the present invention is disclosed a method of preparing a stable dispersion of a medicament in a continuous liquid phase wherein the method comprises (a) combining the medicament, a halogenated alkane propellant, and a $C_{16+}$-unsaturated vegetable oil in an amount sufficient to prevent aggregation of the medicament and (b) agitating the dispersion to completely blend the various components. When the dispersion is a suspension rather than a solution, the medicament must also be milled either before or after combining the components, in order to obtain particles of a desired size. The order of addition may alternatively be varied so that the medicament and the vegetable oil, or the propellant and the vegetable oil, or the medicament and the propellant are first mixed prior to addition of the third component. Preferably, the vegetable oil may be added in an amount of between about 0.001% and about 5% by weight; more preferably, the vegetable oil may be added in an amount of between about 0.01% and about 1% by weight. The propellants, medicaments and vegetable oils suitable for use in the method of the present invention are those described above in connection with the pharmaceutical compositions of this invention.

Another aspect of the invention provides a method of administering a particular medicament to a patient by a pulmonary delivery route, the method comprising inhaling a therapeutically effective amount of a composition according to the invention which contains the particular medicament. Preferred methods of administering generally employ preferred compositions described above.

BRIEF DESCRIPTION OF THE DRAWINGS

FIG. 1 illustrates dosimetry reproducibility of a formulation of the present invention containing 5-LO inhibitor #1 (25 mg/mL) and olive oil (2.5 mg/mL) in the propellant HFC-134a.

FIG. 2 illustrates dosimetry reproducibility of a formulation of the present invention containing 5-LO inhibitor #1 (25 mg/mL) and soybean oil (2.5 mg/mL) in the propellant HFC-134a.

FIG. 3 illustrates dosimetry reproducibility of a formulation of the present invention containing 5-LO inhibitor #1 (25 mg/mL) and safflower oil (2.5 mg/mL) in the propellant HFC-134a.

FIG. 4 illustrates dosimetry reproducibility of a formulation of the present invention containing 5-LO inhibitor #1 (25 mg/mL) and Miglyol™ 829 (2.5 mg/mL) in the propellant HFC-134a.

FIG. 5 illustrates bioavailability of a formulation of the present invention containing 5-LO inhibitor #1 (25 mg/mL) and olive oil (2.5 mg/mL) in the propellant HFC-134a.

DETAILED DESCRIPTION OF THE INVENTION

Figure 1:
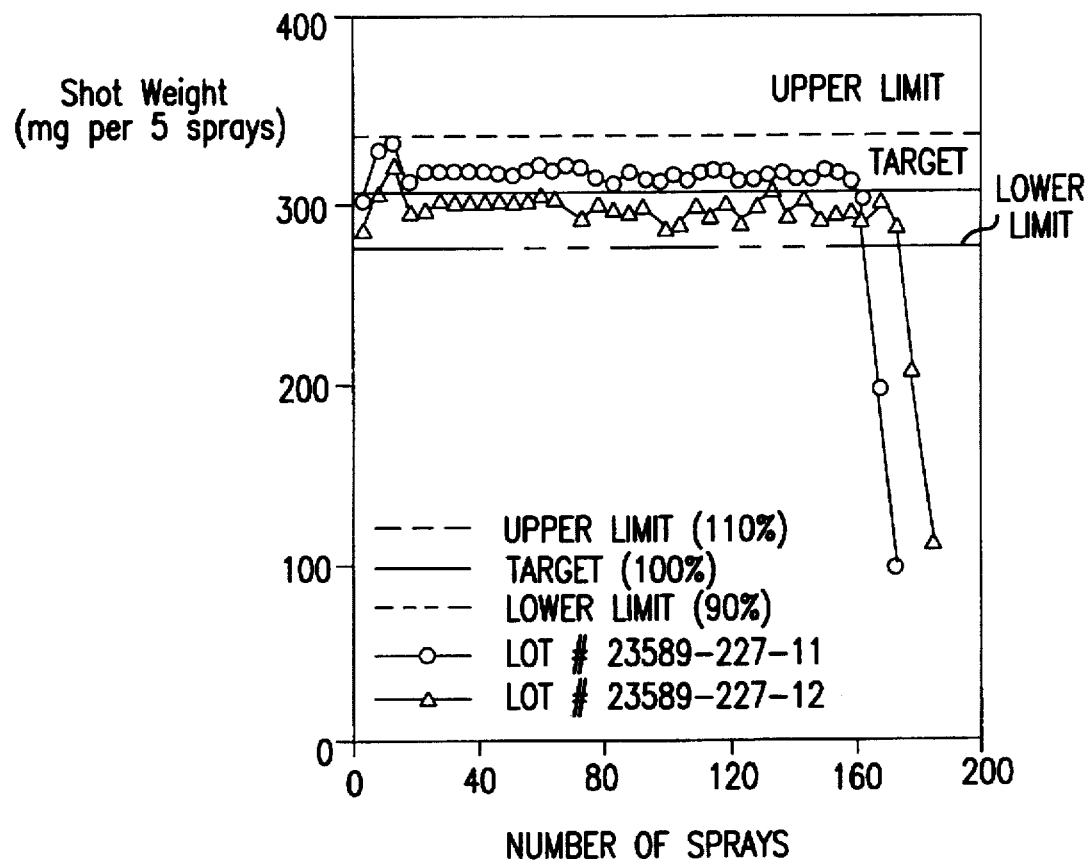

It is expected that both ozone depleting and non-ozone depleting aerosol propellants may be used with the compositions and methods of the present invention. These include for example, the traditionally used chlorofluorocarbons (i.e. Propellant 11 (trichlorofluoromethane), Propellant 12 (dichlorodifluoromethane) and Propellant 114 (dichlorotetrafluoroethane)), as well as other halogenated is given in Table 1 below. Table 1 represents one published listing (from CTFA) of such fatty acid content, though others are available in the literature (e.g. Handbook of Chemistry and Physics, and Merck Index). It will be understood that the precise fatty acid content of each oil will vary somewhat by source and region—as shown by reference to peanut oil or rape seed oil.

TABLE 1

| Type of Oil | % Oleic Acid | % Linoleic Acid | % Linolenic Acid | % Other $C_{16+}$-Unsaturated Acids (>5%) | % Total $C_{16+}$-Unsaturated Acids |
|---|---|---|---|---|---|
| Castor | 5.0 | 4.0 | 0.5 | 87.5 Ricinoleic | 97.0 |
| Corn | 25.0 | 60.0 | 0.5 | 12.0 Palmitic | 97.5 |
| Linseed | 20.0 | 14.5 | 56.0 | 0.0 | 90.5 |
| Mustard Seed (Montana) | 22.0 | 22.5 | 15.5 | 11.5 Eicosenoic, 18.0 Erucic | 89.5 |
| Oiticica | 6.0 | 5.0 | 0.0 | 2.0 Ricinoleic, 76.0 Licanic | 89.0 |
| Olive | 74.0 | 9.0 | 0.5 | 0.0 | 83.5 |
| Peanut (Southwest) | 50.0 | 30.5 | 1.0 | 0.0 | 81.5 |
| Peanut (West Coast) | 38.5 | 38.0 | 1.5 | 0.0 | 78.0 |
| Perilla | 16.0 | 14.0 | 62.0 | 0.0 | 82.0 |
| Rapeseed (High Erucic) | 12.5 | 14.5 | 16.5 | 51.5 Erucic | 95.0 |
| Rapeseed (Montana) | 32.0 | 19.0 | 10.0 | 10.5 Eicosenoic, 23.5 Erucic | 95.0 |
| Rice Bran | 45.5 | 32.0 | 1.0 | 0.0 | 78.5 |
| Safflower | 11.5 | 79.0 | 0.5 | 0.0 | 91.0 |
| Sesame | 41.5 | 43.0 | 0.5 | 0.0 | 85.0 |
| Soybean | 21.0 | 55.5 | 8.5 | 0.0 | 85.0 |
| Sunflower | 17.0 | 72.5 | 0.0 | 0.0 | 89.5 | alkanes, such as HCFC-123 (1,1,1-trifluoro-2,2-dichloroethane), HCFC-124 (1,1,1,2-tetrafluorochloroethane), HCFC-141b, HCFC-225, HFC-125, FC-C51-12 (perfluorodimethylcyclobutane), DYMEL A (dimethyl ether) and DYMEL 152a (1,1-difluoroethane). Of course, for environmental reasons, the preferred propellants are those halogenated alkanes which are non-ozone depleting, such as the hydrofluorocarbons HFC-134a and HFC-227ea. HFC-134a is an especially preferred propellant.

The vegetable oils of the present invention are a diverse, non-specific group of lipophilic substances obtained from non-animal sources. All vegetable oils, despite having different chemical structures and compositions, share the properties of being liquids, water insoluble, and consisting primarily of mixed diglycerides and triglycerides. A "diglyceride" is a diester of glycerol and fatty acids; a "triglyceride" is a triester of glycerol and fatty acids. Like most oils, the oils of the present invention comprise blends of simple and mixed triglycerides. A "simple triglyceride" is a triester of glycerol having three identical fatty acid residues, an example being glyceryl tristearate. A "mixed triglyceride" is a triester of glycerol having fatty acid residues that are not identical. In a mixed triglyceride, the three fatty acid residues may all be different or two may be the same and only one different. An example of a mixed triglyceride having three different fatty acids is glyceryl palmitostearooleate.

Because of their diversity, vegetable oils are typically characterized and classified on the basis of their fatty acid content resulting from saponification. Saponification using hot alkali and acidifying the resulting solution, cleaves the ester linkages to obtain glycerol and a mixture of fatty acids. Vegetable oils of the present invention (termed "$C_{16+}$-unsaturated oils" herein) and are those vegetable oils whose fatty acid composition upon saponification is such that 75% or more of the resulting fatty acids are unsaturated and have a carbon chain length of 16 or greater. The composition of many such oils with regard to the content of $C_{16+}$ fatty acids One other proviso to the vegetable oils used in the present invention, is that they be biocompatible in humans. "Biocompatible" as used herein, refers to those $C_{16+}$-unsaturated oils which are, within the scope of sound medical judgement, suitable for use in contact with the tissues of humans and lower animals without undue toxicity, irritation, allergic response and the like, and are commensurate with a reasonable benefit/risk ratio and are effective for their intended use.

The $C_{16+}$-unsaturated oils of the present invention have Hydrophilic Lipophilic Balance (HLB) values generally below 14 and/or solubility parameters of about 12 or lower and/or dielectric constants of 40 or lower. Generally, the lower the HLB value, the solubility value or dielectric constant of a compound, the more insoluble it is in water. For example, compounds having an HLB of range of 15–20 are generally soluble in water, and those with HLB values of $\leq 5$ are generally insoluble. Thus, as indicated by the values above, the $C_{16+}$-unsaturated oils of the present invention are generally water insoluble. Preferred $C_{16+}$-unsaturated oils have HLB values of between 4 and 10, inclusive. It should be noted that these solubility determinations are well known to those of ordinary skill in the art and may be determined by any method known in the art.

It is also expected that analogs and derivatives of the above $C_{16+}$-unsaturated vegetable oils may be identified which are suitable for use in the compositions and methods of the present invention. To the extent that these analogs and derivatives are similar in structure to or are readily obtained by chemical modification of the vegetable oils, while substantially retaining the physical properties of the vegetable oils, such analogs and derivatives are intended to be included among the compositions and methods of the present invention.

It is expected that the compositions and methods of the invention will be suitable for the administration of a wide variety of peptide and non-peptide drugs. Examples of peptides which may be delivered in this fashion are interferons and other macrophage activation factors, such as lymphokines, muramyl dipeptide (MDP), gamma-interferon, and interferons alpha and beta, and related antiviral and tumoricidal agents; opioid peptides and neuropeptides, such as enkaphalins, endorphins and dynorphins, and related analgesics; renin inhibitors including new-generation anti-hypertensive agents; cholecystokinins (CCK analogs) such as CCK, ceruletide and eledoisin, and related cardiovascular- and CNS-targeting agents; leukotrienes and prostaglandins, such as oxytocin, and related antiinflammatory, oxytocic and abortifacient compounds; erythropoietin and analogs thereof, as well as related haematinics; LHRH analogs, such as leuprolide, buserelin and nafarelin, and related down-regulators of pituitary receptors; parathyroid hormone and other growth hormone analogs; enzymes, such as DNase, catalase and alpha-1 antitrypsin; immunosuppressants such as cyclosporin; GM-CSF and other immunomodulators; and insulin. Such peptides or peptide analogs are frequently not well-absorbed when given orally. Preferred medicaments for use in the formulations of the present invention are leuprolide acetate and 5-LO inhibitor #1.

Non-peptides which may readily be delivered using the formulation compositions and methods of the present invention include virtually any drug or medicament for which a pulmonary delivery route is deemed suitable. Generally categories include bronchodilators, including beta-agonists, such as isoproterenol, albuterol, isoetherine and metaproterenol, and related anti-asthmatics; steroids, such as flunisolide, and similar anti-asthmatics; cholinergic agents, such as cromolyn, and related anti-asthmatics; and 5-lipoxygenase inhibitors (i.e. physiologically active compounds capable of affecting leukotrine biosynthesis, including leukotrine antagonists) and related leukotriene inhibitors. Examples of 5-lipoxygenase inhibitors include zileuton and 5-LO inhibitor #1 described above. Such bronchodilator medicaments may lend themselves to oral administration, but when given by inhalation are found to produce rapid reversal of bronchoconstriction in cases of allergic airway disease and asthma. Also, these compounds may be administered more frequently as MDI formulations than when given orally.

The medicaments useful in the compositions of the present invention include not only those specifically named above, but also where appropriate the pharmaceutically acceptable salts, esters, amides and prodrugs thereof. By "pharmaceutically acceptable salts, esters, amides and prodrugs" is meant those carboxylate salts, amino acid addition salts, esters, amides and prodrugs of a compound which are, within the scope of sound medical judgement, suitable for use in contact with with the tissues of humans and lower animals with undue toxicity, irritation, allergic response and the like, commensurate with a reasonable benefit/risk ratio and effective for their intended use.

In particular, the term "salts" refers to the relatively non-toxic, inorganic and organic acid addition salts of a medicinal compound. These salts can be prepared in situ during the final isolation and purification of the compound or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate and laurylsulphonate salts and the like. These may include cations based on the alkali and alkaline earth metals, such as sodium, lithium, potassium, calcium, magnesium and the like, as well as nontoxic ammonium, quaternary ammonium and amine cations including, but not limited to, ammonium, tetramethylammonium, tetraethylammonium, methylamine, dimethylamine, trimethylamine, triethylamine, ethylamine and the like. (See, for example S. M. Berge, et al., "Pharmaceutical Salts," *J. Pharm, Sci.,* 66:1–19 (1977), incorporated herein by reference.)

Examples of pharmaceutically acceptable, non-toxic esters of a compound include ($C_1$-to-$C_6$ alkyl) esters wherein the alkyl group is a straight or branched chain. Acceptable esters also include ($C_5$-to-$C_7$ cycloalkyl) esters as well as arylalkyl esters such as, but not limited to, benzyl; ($C_1$-to-$C_4$ alkyl) esters are preferred.

Examples of pharmaceutically acceptable, non-toxic amides of medicinal compounds include amides derived from ammonia, primary ($C_1$-to-$C_6$ alkyl) amines and secondary ($C_1$-to-$C_6$ dialkyl) amines wherein the alkyl groups are straight or branched chain. In the case of secondary amines the amine may also be in the form of a 5 - or 6-membered heterocycle containing one nitrogen atom. Amides derived from ammonia, ($C_1$-to-$C_3$ alkyl) primary amides and ($C_1$-to-$C_2$ dialkyl) secondary amides are preferred. Amides of the compounds of the invention may be prepared according to conventional methods.

The term "prodrug" refers to compounds that are rapidly transformed in vivo to yield the parent medicinal compound, as for example by hydrolysis in blood. A thorough discussion is provided in T. Higuchi and V. Stella, "Pro-drugs as Novel Delivery Systems", Vol 14 of the A.C.S. Symposium Series, and in *Bioreversible Carriers in Drug Design*, ed. Edward B. Roche, American Pharmaceutical Association and Pergamon Press (1987), both of which are incorporated herein by reference.

When used in the above compositions, a therapeutically effective amount of a medicament of the present invention may be employed in pure form or, where such forms exist, in pharmaceutically acceptable salt, ester or prodrug form. By a "therapeutically effective amount" of a medicament is meant a sufficient amount of the compound to obtain the intended therapeutic benefit, at a reasonable benefit/risk ratio applicable to any medical treatment. It will be understood, however, that the total daily usage of the medicaments and compositions of the present invention will be decided by the attending physician within the scope of sound medical judgement. The specific therapeutically effective dose level for any particular patient and medicament will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific medicament employed; the duration of the treatment; drugs used in combination or coincidental with the specific compound employed; and like factors well known in the medical arts. For example, it is well within the skill of the art to start doses at levels lower than required to achieve the desired therapeutic effect and to gradually increase the dosage until the desired effect is achieved.

The total daily doses of the medicaments contemplated for use with this invention, and consequently the concentrations by weight of the medicaments in the respective compositions, may vary widely, but are within the typical skill of the routine practitioner. In the case of an LHRH analog, such as leuprolide acetate, the intended daily dose may range from about 0.01 to about 5 mg/day; accordingly, where an aerosol inhaler is to be used several times a day with a discharge volume of between about 5 and about 250 µL, the concentration of medicament will be between about 0.2 and about 20 mg/mL. Similarly, in the case of a 5-lipoxygenase inhibitor expected to be administered in a daily dose ranging from about 0.01 to about 10 mg/kg/day, the concentration will be between about 0.001 and about 100 mg/mL. Of course, medicament concentrations outside of these ranges may also be suitable, where different potencies, dosing frequencies and discharge volumes are used.

The compositions of the invention may be prepared by combining the vegetable oil with a medicament which has been milled or otherwise reduced to a desired particle size, and placing the mixture in a suitable aerosol container or vial. After sealing the container, an aerosol propellant is introduced and the system is agitated to fully blend the ingredients. Alternatively, the vegetable oil and medicament may be milled together after addition of propellant. In some instances, it may be necessary to wet-mill the medicament in a closed system, as for example under temperature and pressure conditions which permit the medicament to be milled while mixed with a liquid-phase aerosol propellant. It is expected that, for any particular combination of medicament, propellant and vegetable oil, the ideal order of addition of ingredients and the conditions under which they are to be combined may readily be determined.

In addition to suspension formulations, the compositions of the invention may be prepared as solutions. Similar to the suspension formulations, solution formulations may be prepared by combining the vegetable oil, a medicament and a propellant in any manner described above, but without the step of milling. Thus the only requirement is to blend the components, whether they are combined in a single step (i.e. altogether) or in multiple steps. When the components are combined in multiple steps, the solution must be agitated after each addition to thoroughly blend the components.

The compositions and methods of the present invention will be better understood in connection with the following examples, which are intended as an illustration of and not a limitation upon the scope of the invention. Both below and throughout the specification, it is intended that citations to the available literature are expressly incorporated by reference.

EXAMPLE 1

General procedures

A. Analytical Method for 5-LO Inhibitor #1

All quantitative analyses for 5-LO inhibitor #1 formulations were performed by high pressure liquid chromatography (HPLC). The mobile phase composition was 30% v/v tetrahydrofuran in water with 0.128% w/v tetramethylammonium perchlorate and 0.075% v/v trifluoroacetic acid. A Regis Little Champ™ C-18, 4.6×50 mm column was used. The mobile phase flow rate was maintained at 1.0 milliliters/minute (mL/min). Detection wavelength was set at 282 nanometers (nm) and typical injection volumes were between 25 to 50 microliters (µL). Under these conditions, the standard curve for the parent drug was linear between the range of 3 to 75 micrograms/milliliter (µg/mL) ($r^2 \geqq 0.990$), with a run time of about 8 minutes.

B. Preparation of MDI Formulations for Performance Testing

MDI formulations for performance testing were prepared in the following manner: For each test formulation, about 5 mL (or 7.4 grams) of glass beads were placed into a suitable glass aerosol container (vial), along with 100 mg to 250 mg drug and a vegetable oil in the amounts needed to produce the desired final concentrations. All vegetable oils used in the following examples were purchased from Sigma® Chemical Company (St. Louis, Mo., 63178). The vials were crimped shut with valves having delivery values (volumes per spray) of 50 µL, and then charged with 10 mL of HFA-134a propellant. The filled vials were then shaken for 24 hours at about 50 cycles/minute to mill and disperse the drug. The vials were observed for dispersion integrity and any distinct signs of instability (e.g. color change and/or gross aggregation). The formulations were then used in the in vitro or in vivo studys described below.

Miglyol™ 829 (Dyanmite Noble of America) was also prepared in the manner described above for use as a control. Miglyol™ 829 is a fractionated coconut oil containing glyceryl esters of $C_8$–$C_{10}$ fatty acids. Its density is close to that of water. Miglyol™ 829 complies with the requirements of a food additive regulated under 21 CFR 182.860.

EXAMPLE 2

Physical Stability of MDI Formulations Containing Vegetable Oils and a Medicant A determination of the effect of vegetable oils on the physical stability of several MDI formulations prepared with HFA-134a was conducted as follows: A vegetable oil was combined either with (1) leuprolide acetate (Table 2a) or (2) 5-LO inhibitor #1 (Table 2b) in the amounts indicated and placed in appropriate transparent aerosol containers (vials). (Leuprolide acetate and its preparation are described in U.S. Pat. No. 4,005,063, issued Jan. 25, 1977, which is incorporated herein by reference. 5-LO inhibitor #1 and its preparation are described in U.S. Pat. No. 5,288,751, issued Feb. 22, 1994, also incorporated by reference). Additionally, a surfactant was added to some of the vials in an amount to produce a final concentration of 1% by weight. The vials were crimped and charged with approximately 10 mL of HFC-134a and agitated to blend the ingredients. The dispersion quality in each preparation was evaluated visually after 24 hours using the following criteria:

Poor: Phase separation; top phase clear, bottom phase containing solids

Fair: Partial phase separation; cloudiness in the top phase

Good: Grainy appearance; no phase separation

Clear: Clear solution

Results of these tests are shown below in Tables 2a and 2b. The data obtained show that the formulations of the present invention maintain a high degree of dispersion even after 24 hours. By comparison, control formulations of each of the test compounds (which were prepared without vegetable oils) are seen to have unacceptable dispersion quality (which was evident in each case after less than 30 seconds).

TABLE 2a

Dispersion Quality of Leuprolide Acetate in HFA-134a

| Excipient 1 | Excipient 2 | Leuprolide Acetate | Dispersion Quality (measured after 24 Hours) |
|---|---|---|---|
| — | — | 1% | Poor |
| — | | 1% | Poor |
| 0.1% Span 20™ | 0.05% | — | Clear |
| 0.1% Span 20™ | 0.10% | 1% | Moderately |

TABLE 2a-continued

Dispersion Quality of Leuprolide Acetate in HFA-134a

| Excipient 1 | Excipient 2 | Leuprolide Acetate | Dispersion Quality (measured after 24 Hours) |
|---|---|---|---|
| | | | Acceptable Dispersion |
| 0.1% Span 60 ™ | — | — | Clear |
| 0.1% Span 60 ™ | — | 1% | Poor |
| 0.1% Span 85 ™ | — | — | Clear |
| 0.1% Span 85 ™ | — | 1% | Poor |
| 0.5% Cholesterol | — | — | Poor |
| 0.5% Cholesterol | — | 1% | Good |
| 0.5% DSA[a] | — | — | Poor |
| 0.5% DSA | — | 1% | Good |
| 0.3% Olive Oil | — | — | Clear |
| 0.3% Safflower Oil | — | — | Clear |
| 0.3% Soybean Oil | — | — | Clear |
| 0.1% Olive Oil | — | 1% | Good |
| 0.1% Safflower Oil | — | 1% | Good |
| 0.1% Soybean Oil | — | 1% | Good |
| 0.1% Olive Oil | 1% Span 85 ™ | — | Clear |
| 0.1% Safflower Oil | 1% Span 85 ™ | — | Clear |
| 0.1% Soybean Oil | 1% Span 85 ™ | — | Clear |
| 0.1% Olive Oil | 1% Span 85 ™ | 1% | Clear |
| 0.1% Safflower Oil | 1% Span 85 ™ | 1% | Clear |
| 0.1% Soybean Oil | 1% Span 85 ™ | 1% | Clear |
| 0.1% Span 20 ™ | 0.1% Cholesterol | 1% | Moderately acceptable dispersion |
| 0.1% Span 20 ™ | 0.1% DSA | | Poor |
| 0.1% Span 60 ™ | 0.1% DSA | | Poor |
| 0.1% Span 85 ™ | 0.1% DSA | | Poor |

[a]DSA refers to decane sulfonic acid

TABLE 2b

Dispersion Quality of 5-LO Inhibitor #1 in HFA-134a

| Excipient 1 | Excipient 2 | 5-LO Inhibitor | Dispersion Quality (measured after 24 Hours) |
|---|---|---|---|
| — | — | 1% | Poor |
| — | — | 1% | Poor |
| 0.1% Span 20 ™ | — | 1% | Moderately clear |
| 0.1% Span 85 ™ | — | 1% | Moderately clear |
| 0.1% Cholesterol | — | 1% | Poor |
| 0.3% Cholesterol | — | 1% | Poor |
| 0.5% Cholesterol | — | 1% | Poor |
| 0.3% DSA[a] | — | 1% | Poor |
| 0.5% DSA | — | 1% | Poor |
| 0.1% SLS[b] | — | 1% | Poor |
| 0.3% SLS | — | 1% | Poor |
| 0.5% SLS | — | 1% | Poor |
| 0.1% Span 60 ™ | — | 1% | Poor |
| 0.1% Olive Oil | — | 1% | Clear |
| 0.1% Safflower Oil | — | 1% | Clear |
| 0.1% Soybean Oil | — | 1% | Clear |
| 0.1% Oleic Acid | — | 1% | Poor |
| 0.1% Olive Oil | 0.1% Span 85 ™ | 1% | Clear |
| 0.1% Safflower Oil | 0.1% Span 85 ™ | 1% | Clear |
| 0.1% Soybean Oil | 0.1% Span 85 ™ | 1% | Clear |
| 0.1% Labrafac | — | 1% | Poor |
| 0.3% Labrafac | — | 1% | Poor |
| 0.1% Labrafac | 1% Span 85 ™ | .1% | Clear |
| 0.1% Span 85 ™ | 0.1% DSA | 1% | Clear |
| 0.1% Span 85 ™ | 0.1% SLS | 1% | Clear |
| 0.1% Span 85 ™ | 0.1% Cholesterol | 1% | Clear |

TABLE 2b-continued

Dispersion Quality of 5-LO Inhibitor #1 in HFA-134a

| Excipient 1 | Excipient 2 | 5-LO Inhibitor | Dispersion Quality (measured after 24 Hours) |
|---|---|---|---|
| 0.1% SLS | 0.1% Cholesterol | 1% | Poor |
| 0.2% SLS | 0.2% Cholesterol | 1% | Moderately acceptable dispersion |
| 0.1% DSA | 0.1% Cholesterol | 1% | Poor |

[a]DSA refers to decane sulfonic acid
[b]SLS refers to sodium lauryl sulfate

EXAMPLE 3

Effect of Dispersant Type on Dose Reproducibility as Measured by Mean Shot Weight Gravimetric measurements of serially actuated shots of a test MDI formulation are a type of performance testing which provide a quick indication of dose reproducibility. Formulation shot weight delivered from a vial is a function of valve capacity (volume) and the density of the formulation. The density of HFC-134a is about 1.22 grams/milliliter (See Dalby, R., "Defining Acceptable Standards For MDIs Formulated With New Propellants", *Respiratory Drug Delivery III*, Williamsburg, Va., May 16–22, 1992). Therefore, a 50 μL valve should theoretically deliver about 61 milligrams (mg)/spray or 305 mg/5 sprays. Typical acceptance limits fall within a ±10% range. Thus, for a formulation with a 50 μL valve, acceptable shot weight limits are about 274.5 to 333.5 mg/5 sprays.

Dose reproducibility using the compositions of the invention containing 5-LO inhibitor #1 and a vegetable oil (or Miglyol™ 829 as a control) was tested as follows: Vials were prepared as described in (B) above. Each vial was shaken and its valve primed by aerosolizing 5 times in succession, after which the vial was weighed. The valve of each vial was then actuated five times, followed by another weighing. This process was repeated until shot weights started dropping off appreciably.

Figure 2:
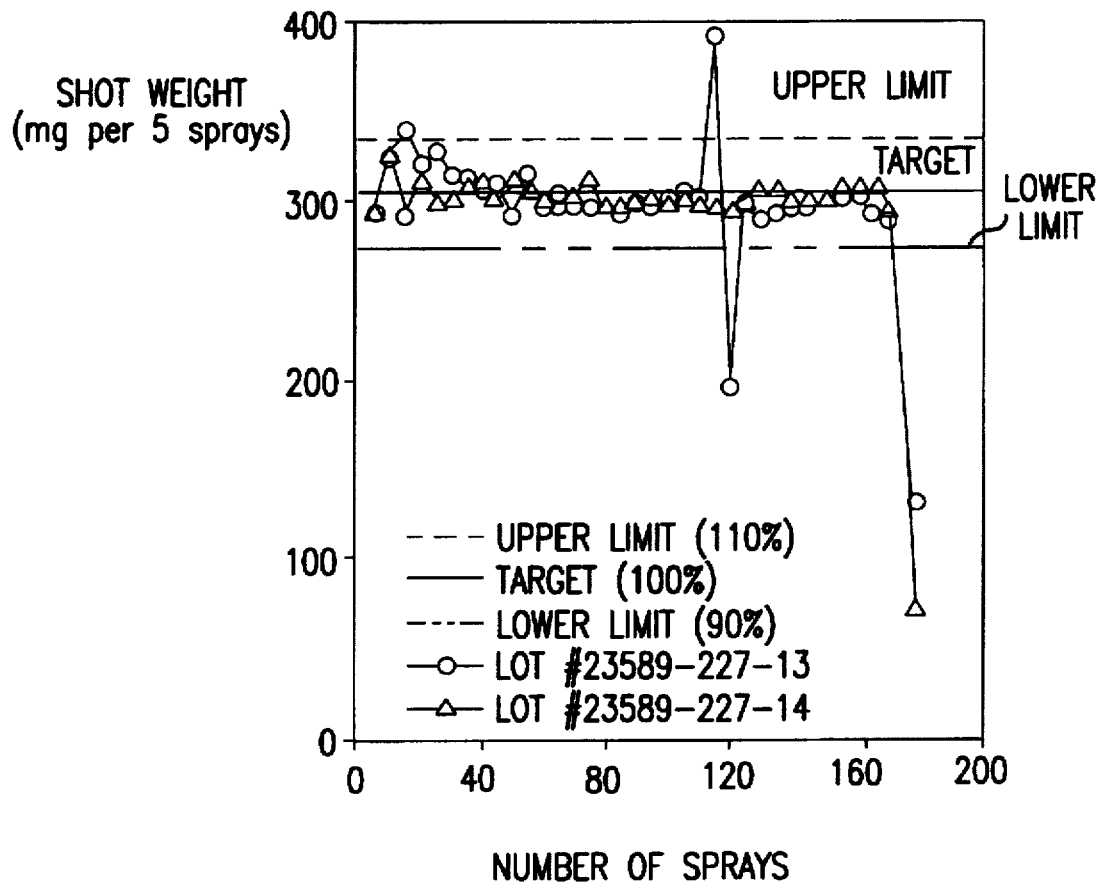
Figure 3:
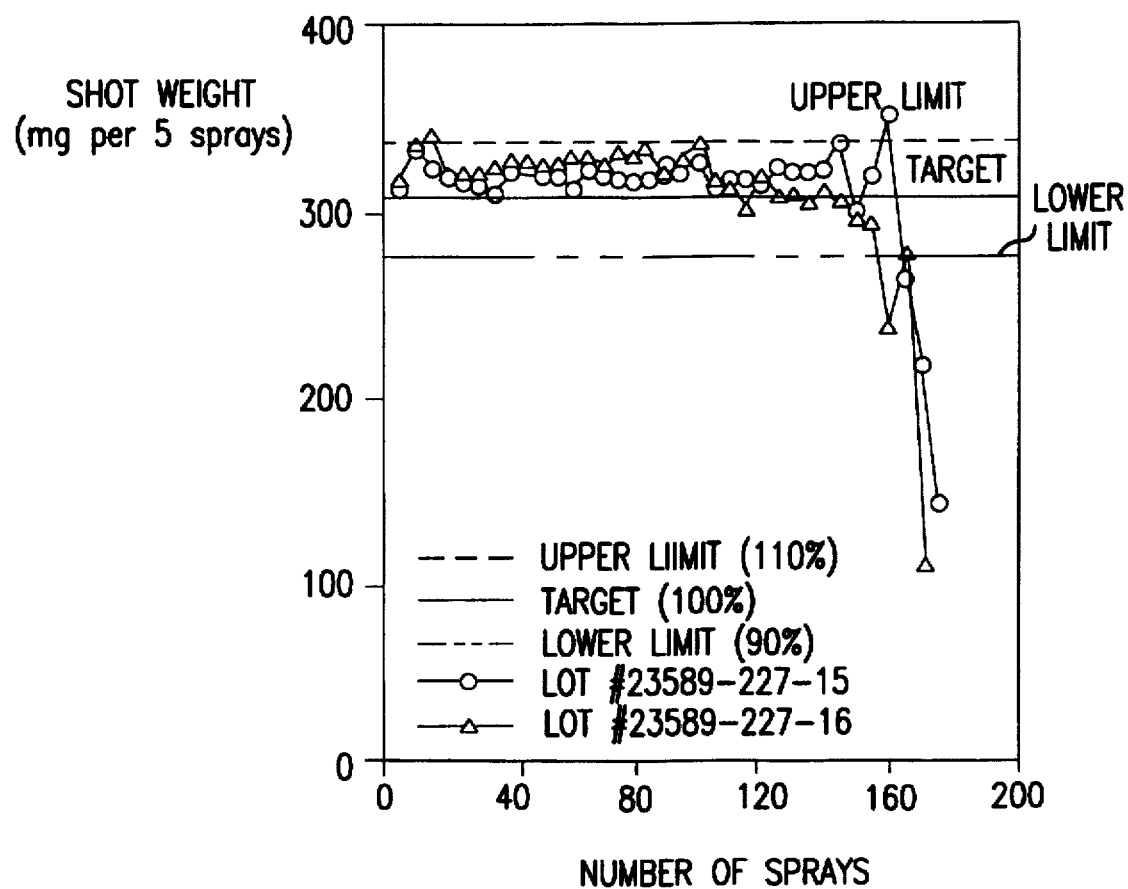
Figure 4:
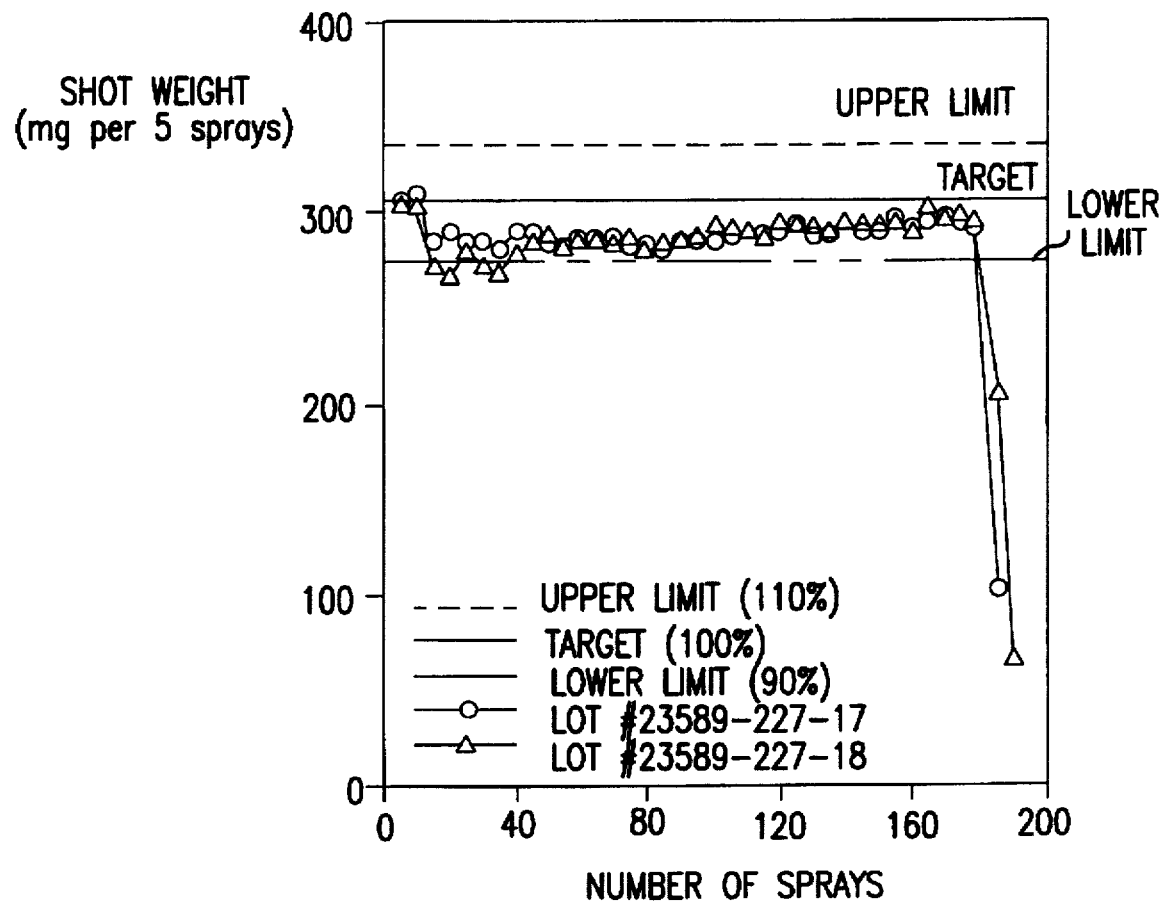

FIGS. 1, 2, and 3 show shot weight profiles from vials containing 25 mg/mL 5-LO inhibitor #1 and 2.5 mg/mL of olive oil, soybean oil, and safflower oil respectively. FIG. 4 shows the shot weight profile from vials containing 25 mg/mL 5-LO inhibitor #1 and 2.5 mg/mL of the control, Miglyol™ 829. As seen in the Figures, all oil formulations produced shot weights within acceptance limits of 90–110% of the label (i.e. theoretical) claim. As also shown, acceptable dosimetry from these vials lasted through about spray #160. Thus, including the 5 spray shots for priming the valve, approximately 8.25 mL of formulation was found to be deliverable from a container with a 10 mL fill volume. The remaining 1.75 mL of (or approximately 17.5% of the initial fill volume) was non-deliverable due to substantial reduction in internal pressure.

Table 3 summarizes the shot weight data of FIGS. 1, 2, 3 and 4 and demonstrates the uniformity with which the compositions of the present invention are delivered by a MDI device.

TABLE 3

Shot Weight Data for 5-LO Inhibitor #1 (25 mg/mL)
Containing 2.5 mg/mL Vegetable Oils in HFC-134a

| Lot # 23589- | Dispersant | Shot Weight (mg/5 sprays) Mean ± SD[a] (n = 33 to 36) | Failures in Shot Weight[b] |
|---|---|---|---|
| 227-11 | Olive Oil | 314.2 ± 5.9 | 0/33 (0%)[c] |
| 227-12 | Olive Oil | 295.7 ± 7.2 | 0/35 (0%) |
| 227-13 | Soybean Oil | 303.2 ± 26.9 | 3/34 (8.82%) |
| 227-14 | Soybean Oil | 303.4 ± 6.94 | 0/34 (0%) |
| 227-15 | Safflower Oil | 318.4 ± 9.0 | 1/32 (3.13%) |
| 227-16 | Safflower Oil | 315.2 ± 20.2 | 2/33 (6.06%) |
| 227-18 | Miglyol™ 829 | 288.9 ± 6.5 | 0/36 (0%) |
| 227-19 | Miglyol™ 829 | 287.9 ± 9.3 | 4/36 (11.1%) |

[a]SD refers to standard deviation.
[b]Failures in shot weights represent the number of times the shot weight measurement fell outside the 90–110% limit. The target mean shot weight for 5 sprays was 305 mg; the 90–110% limits were 274.5–335.5 mg.
[c]The numbers in parentheses refer to percent failures.

The drug content uniformity, depicted in Table 4, shows the amount of drug (in milligrams) delivered per 10 sprays. As the results show, mean dosimetry of the formulation containing 2.5 mg olive oil was about 104% of the label (i.e. theoretical) claim. The other formulations delivered 94–97% of the label claim. All results fell within the ±10% acceptance limits and indicate satisfactory performance of the delivery device.

TABLE 4

Unit Spray Content of Formulations Containing 25 mg/mL
5-LO Inhibitor #1 and a Vegetable Oil in HFC-134a

| Lot #23589- | Units Spray Content (mg/10 sprays) | | |
|---|---|---|---|
| | Actual | Theoretical | % of Theoretical |
| A. Olive Oil | — | — | — |
| 227-11 | 13.48 | 12.41 | 108.60 |
| 227-12 | 13.70 | 13.78 | 99.42 |
| Mean ± SEM | 13.59 ± 0.11 | 13.10 ± 0.69 | 104.01 ± 4.59 |
| B. Soybean Oli | — | — | — |
| 227-13 | 12.10 | 13.21 | 91.57 |
| 227-14 | 12.25 | 12.69 | 96.50 |
| Mean ± SEM | 12.18 ± 0.08 | 12.95 ± 0.26 | 94.04 ± 2.47 |
| C. Safflower Oil | — | — | — |
| 227-15 | 12.54 | 13.76 | 91.11 |
| 227-16 | 12.07 | 12.44 | 96.99 |
| Mean ± SEM | 12.31 ± 0.24 | 13.10 ± 0.66 | 94.05 ± 2.94 |
| D. Miglyol™ 829 | — | — | — |
| 227-17 | 11.82 | 12.35 | 95.70 |
| 227-18 | 13.25 | 13.43 | 98.68 |
| Mean ± SEM | 12.54 ± 0.72 | 12.89 ± 0.54 | 97.19 ± 1.49 |

EXAMPLE 4

Content Uniformity of MDI Delivery of Compositions Containing 5-LO Inhibitor #1

Content uniformity, (a second type of performance test) was evaluated as follows: Vials were prepared according to Example 1B above using 5-LO inhibitor #1 either with a vegetable oil or with Miglyol™ 829 as a control. Each vial was shaken and its valve primed by aerosolizing 5 times in succession, after which the vial was weighed. Thereafter, a defined number of sprays were made consecutively while immersing the valve stem in a beaker containing 25 mL ethanol. The contents of the solution were gently swirled to disperse the drug to homogeneity. The resulting dispersion was diluted with a methanol:water solution (1:1 v/v) and assayed for drug content by high performance liquid chromatography (HPLC).

EXAMPLE 5

Bioavailability of MDI Compositions Containing Olive Oil

Using a test preparation containing 25 mg/mL 5-LO inhibitor #1 and 2.5 mg/mL olive oil in HFC-134a propellant, pulmonary absorption and in vivo distribution (i.e. bioavailibility factors) were assessed in four tracheostomized dogs (Marshall Farms, N.Y.) weighing about 10 kilograms (kg) each. Four sprays, delivering 1.25 mg of active 5-LO inhibitor #1/spray, were delivered to the trachea of each dog, resulting in a total drug dose of about 0.5 mg/kg. Blood samples were collected at 0.25, 0.5, 1, 2, 3.5, 5, 7, 9, 12 and 24 hours after dosing and the plasma assayed for drug concentration using the HPLC method described in Example 1A above. This data was compared with bioavailability data obtained from a previous study where tracheostomized dogs received by intravenous injection (i.v.) 0.5 mg/kg of 5-LO inhibitor #1 in an aqueous formulation.

Figure 5:
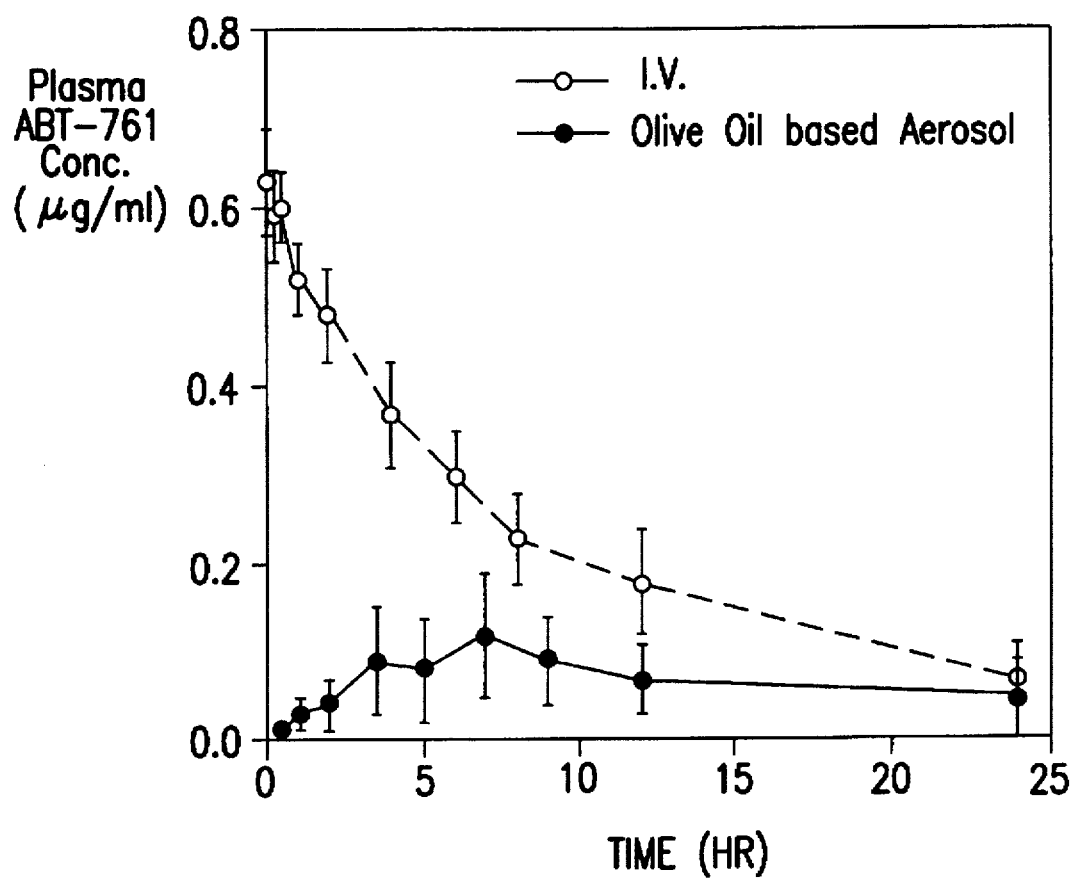

The results of these studies, as shown in Tables 5a and 5b and in FIG. 5, demonstrate that drugs are effectively administered using the MDI formulations of the present invention. Table 5a and FIG. 5 summarize the plasma drug concentrations over 24 hours following inhalation delivery of about 0.5 mg/kg 5-LO inhibitor #1. The results showed fast onset of drug absorption (e.g. 0.03 µg/mL within 1 hour of dosing). In addition, drug levels were maintained at ≧0.07 µg/mL for at least 12 hours after dosing. As shown by the historical data, i.v. delivery of 5-LO inhibitor #1 declines rapidly from about 0.6 µg/mL at 0.25 hours to about 0.2 µg/mL by 12 hours after dosing. In the case of the inhalation formulation however, drug absorption continued for about 6 to 8 hours after dosing suggesting that sustained systemic drug delivery from the lung is possible.

TABLE 5a

Plasma Concentrations Following IV and Inhalation Delivery of 5-LO Inhibitor #1 to Tracheostomized Dogs

| Time (hours) | 5-LO Inhibitor Levels (µg/mL) | |
|---|---|---|
| | i.v.* (n = 7–9) | Inhalation (n = 4) |
| 0.00 | 0 | 0 |
| 0.08 | 0.63 ± 0.06$^a$ | N.D.$^c$ |
| 0.25 | 0.59 ± 0.05$^a$ | 0.00 ± 0.00 |
| 0.50 | 0.60 ± 0.04$^a$ | 0.01 ± 0.01 |
| 1.00 | 0.52 ± 0.04$^a$ | 0.03 ± 0.02 |
| 2.00 | 0.48 ± 0.05$^b$ | 0.04 ± 0.03 |
| 3.50 | N.D. | 0.09 ± 0.06 |
| 4.00 | 0.37 ± 0.06$^b$ | N.D. |
| 5.00 | N.D. | 0.08 ± 0.06 |
| 6.00 | 0.30 ± 0.05$^a$ | N.D. |
| 7.00 | N.D. | 0.12 ± 0.07 |
| 8.00 | 0.23 ± 0.05$^a$ | N.D. |
| 9.00 | N.D. | 0.09 ± 0.05 |
| 12.00 | 0.18 ± 0.06$^b$ | 0.07 ± 0.04 |
| 24.00 | 0.07 ± 0.02$^a$ | 0.05 ± 0.06 |

*i.v.: Dose was 5 mL of 1 mg/mL 5-LO inhibitor #1 in 60% v/v polyethylene glycol 400 in water.
$^a$Values shown represent the mean ± standard deviation of 9 animals.
$^b$Values shown represent the mean ± standard deviation of 7 animals.
$^c$N.D. = Not determined.

A summary of the pharmacokinetic parameters is presented in Table 5b. As is shown in the Table, the inhalation formulation displayed rapid onset and prolonged absorption of drug from the lungs. After correcting for non-absorptive losses occurring within the nozzle of the device or from deposition of the medicament in the pharynx (and which typically account for at least 50% of the drug released), the absolute lung bioavailability of 5-LO inhibitor #1 was estimated to be about 64% of that achieved by i.v. administration.

TABLE 5b

Pharmacokinetic Summary Following Inhalation Delivery of 0.5 mg/kg 5-LO Inhibitor #1 to Tracheostomized Dogs

| | Formulation Type | |
|---|---|---|
| Parameter | i.v.$^a$ (n = 7–9) | Inhalation (n = 4) |
| Concentration$_{max}$ (µg/mL) | — | 0.15 ± 0.03 |
| Time$_{max}$ (hr) | — | 10.38 ± 9.23 |
| AUC$_{0-24}$ (ug*hr/mL) | 5.06 ± 1.04 | 1.60 ± 0.40 |
| Bioavailability | — | 64% |

$^a$As in Table 5a.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the substituents, means of preparation and/or methods of use of the invention, may be made without departing from the spirit and scope thereof.

What is claimed is:

1. A pharmaceutical composition for aerosol delivery comprising a medicament suitable for pulmonary delivery, a halogenated alkane propellant and a biocompatible $C_{16+}$ unsaturated vegetable oil having an HLB value of less than 14, wherein the medicament is present in a concentration of from about 0.05% to about 5% by weight, the vegetable oil is present in a concentration of from 0.001% to about 10% by weight, the halogenated alkane propellant is selected from the group consisting of HCFC 123, HCFC 124, HCFC 141b, HCFC 225, HCFC 125, perfluorodimethylcylobutane, DYMEL 152a, HFC 134a and HFC 227ea and the biocompatible $C_{16+}$ unsaturated vegetable oil is selected from olive oil, safflower oil and soybean oil.

2. A pharmaceutical composition according to claim 1 wherein the halogenated alkane is selected from the group consisting of HFC-134a and HFC-227ea.

3. A pharmaceutical composition according to claim 2 wherein the biocompatible $C_{16+}$-unsaturated vegetable oil is present in a concentration of between about 0.002% and about 5% by weight.

4. A pharmaceutical composition according to claim 1 wherein the medicament is a peptide.

5. A pharmaceutical composition according to claim 4 wherein the peptide is selected from the group consisting of interferons, opioid peptides, neuropeptides, renin inhibitors, cholecystokinins, leukotrienes, prostaglandins, LHRH analogs, immunosuppressants, growth hormones, erthropoietin and analogs thereof.

6. A pharmaceutical composition according to claim 5 wherein the peptide is an LHRH analog selected from leuprolide, delhirelix, cetrorelix, goserelin buserelin, nafarelin and Ac-D-2-Nal-D-4-ClPhe-D-3-Pal-Ser-N-MeTyr-D-Lys(Nic)-Leu-Lys(N-Isp)-Pro-D-Ala-NH$_2$.

7. A pharmaceutical composition according to claim 5 wherein the peptide is an immunosuppressant selected from cyclosporin A, cyclosporin B, cyclosporin G, rapamycin, ascomycin and tacrolimus.

8. A pharmaceutical composition according to claim 5 in which the propellant is a non-ozone depleting non-chlorofluorocarbon.

9. A pharmaceutical composition according to claim 1 wherein the medicament is selected from the group consisting of 5-lipoxygenase inhibitors, antiallergens, mucolytics, steroids, and bronchodilators including β-adrenergics.

10. A pharmaceutical composition according to claim 9 wherein the medicament is a β-adrenergic selected from isoproterenol, albuterol, metaproterenol, terbutaline, isoetherine, epinephrine and phenylephrine.

11. A pharmaceutical composition according to claim 9 wherein the medicament is a mucolytic selected from ipratropium, cromolyn and DNase.

12. A pharmaceutical composition according to claim 9 wherein the medicament is N-[3-[5-(4-fluorophenylmethyl)-2-thienyl]-1-methyl-2-propynyl]-N-hydroxyurea.

13. A pharmaceutical composition according to claim 9 wherein the biocompatible $C_{16+}$-unsaturated vegetable oil is present in a concentration of between about 0.01% and about 1% by weight.

14. A pharmaceutical composition according to claim 1 wherein said medicament is selected from N-[3-[5-(4-fluorophenylmethyl)-2-thienyl]-1-methyl-2-propynyl]-N- hydroxyurea and leuprolide acetate, and wherein said medicament is present in a concentration between about 0.05% and about 5% by weight and said biocompatible $C_{16+}$-unsaturated vegetable oil is present in a concentration between about 0.01% and about 1% by weight, and further comprising aspartame in a concentration between about 0.02% and about 0.5% by weight and menthol in a concentration between about 0.01 and about 0.25% by weight.

15. A pharmaceutical composition according to claim 14 wherein said medicament is present in a concentration between about 0.125% and about 2.5% by weight, said biocompatible $C_{16+}$-unsaturated vegetable oil is present in a concentration between about 0.1% and about 0.5% by weight, said aspartame is present in a concentration between about 0.05% and about 0.2% by weight, and said menthol is present in a concentration between about 0.025 and about 0.1% by weight.

* * * * *

UNITED STATES PATENT AND TRADEMARK OFFICE
CERTIFICATE OF CORRECTION

PATENT NO. : 5,635,161
DATED : June 3, 1997
INVENTOR(S) : Adjei et al.

It is certified that error appears in the above-indentified patent and that said Letters Patent is hereby corrected as shown below:

Column 16, line 16, change "perfluorodimethylcylobutane" to -- perfluorodimethylcyclobutane--.

Signed and Sealed this

Second Day of September, 1997

Attest:

BRUCE LEHMAN

Attesting Officer

Commissioner of Patents and Trademarks